(12) United States Patent
Baxter, III et al.

(10) Patent No.: US 7,947,052 B2
(45) Date of Patent: May 24, 2011

(54) SUTURING DEVICE WITH ANGLED HEAD

(75) Inventors: Chester O. Baxter, III, Loveland, OH (US); James J. Bedi, Cincinnati, OH (US); Lawrence Crainich, Charlestown, NH (US); Robert C. Allman, Charlestown, NH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 918 days.

(21) Appl. No.: 11/521,580

(22) Filed: Sep. 15, 2006

(65) Prior Publication Data

US 2008/0071295 A1    Mar. 20, 2008

(51) Int. Cl.
*A61B 17/04* (2006.01)
(52) U.S. Cl. .................... 606/144; 606/139
(58) Field of Classification Search .............. 606/144, 606/145, 139, 1, 170, 174, 205, 130; 112/169, 112/80.03; 223/104; 623/2.11
See application file for complete search history.

(56) References Cited

U.S. PATENT DOCUMENTS

| | | | | |
|---|---|---|---|---|
| 662,004 A | * | 11/1900 | Lawrence | 112/80.03 |
| 793,674 A | * | 7/1905 | Mayer | 112/80.03 |
| 5,308,353 A | * | 5/1994 | Beurrier | 606/144 |
| 5,549,617 A | * | 8/1996 | Green et al. | 606/144 |
| 5,628,446 A | * | 5/1997 | Geiste et al. | 227/175.1 |
| 5,709,693 A | * | 1/1998 | Taylor | 606/145 |
| 5,993,466 A | * | 11/1999 | Yoon | 606/147 |
| 7,338,434 B1 | * | 3/2008 | Haarstad et al. | 600/37 |
| 7,338,504 B2 | * | 3/2008 | Gibbens et al. | 606/144 |
| 2002/0193809 A1 | | 12/2002 | Meade et al. | |
| 2003/0055436 A1 | * | 3/2003 | Daum et al. | 606/130 |
| 2003/0233104 A1 | | 12/2003 | Gellman et al. | |
| 2006/0041263 A1 | | 2/2006 | Chu et al. | |

FOREIGN PATENT DOCUMENTS

WO    WO 2004/086986    10/2004

\* cited by examiner

*Primary Examiner* — (Jackie) Tan-Uyen T Ho
*Assistant Examiner* — Alexander Orkin
(74) *Attorney, Agent, or Firm* — Welsh Flaxman & Gitler LLC

(57) ABSTRACT

A suturing apparatus for the continuous application of a suture includes a suturing head shaped and dimensioned for attachment to a distal end of a support member. The suturing head includes a track shaped and dimensioned for receiving a needle for movement about the track. A support arm includes first and second lateral arms connected by a central connecting member supporting the track. The support arm includes a longitudinal axis and the track lies in a transverse plane. Angular orientation of the support arm relative to the track is achieved by positioning the transverse plane of the track at an oblique angle relative to the longitudinal axis of the support arm such that operators are provided with improved access to the surgical site. A drive assembly is coupled to the needle for controlled movement about the track.

18 Claims, 7 Drawing Sheets

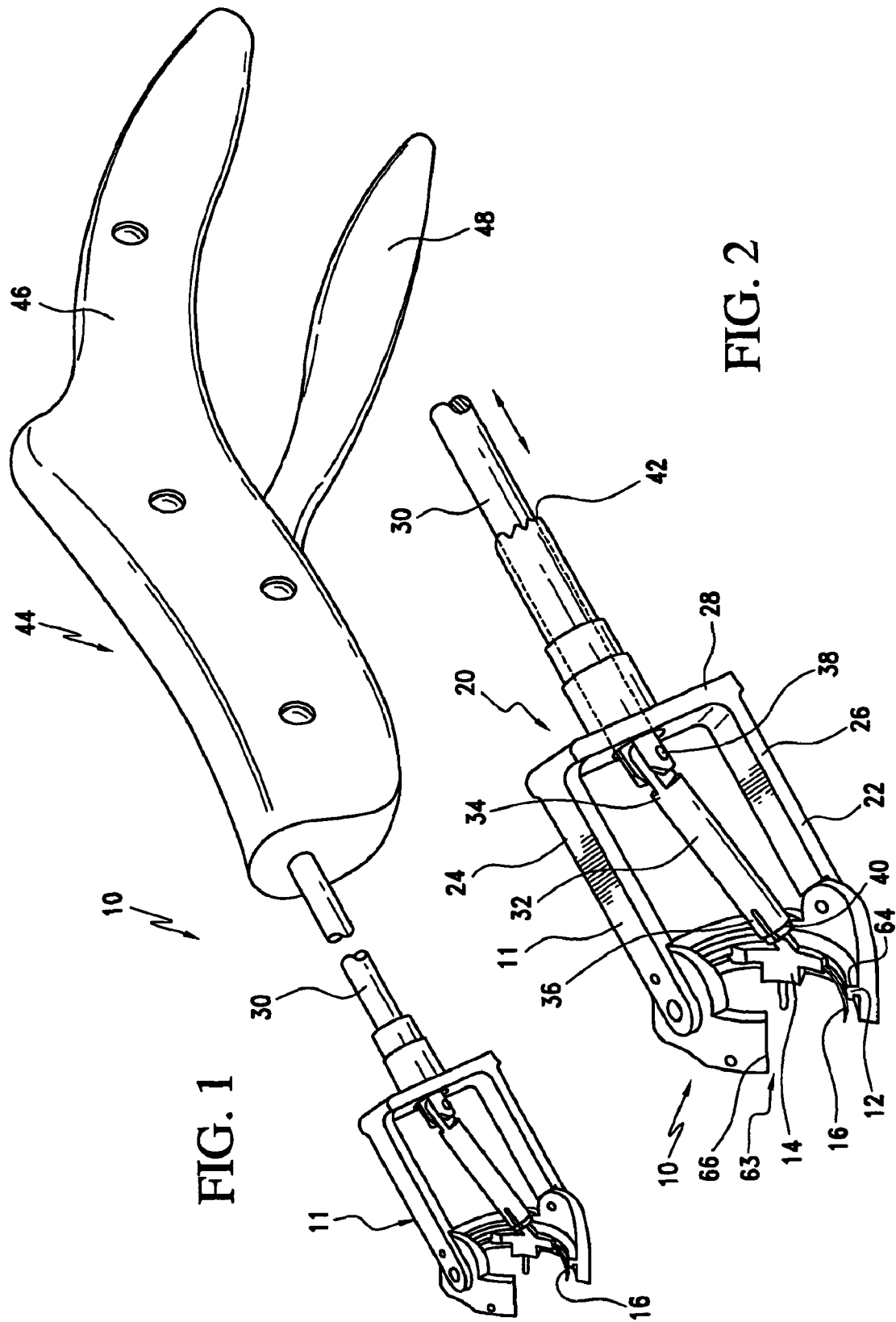

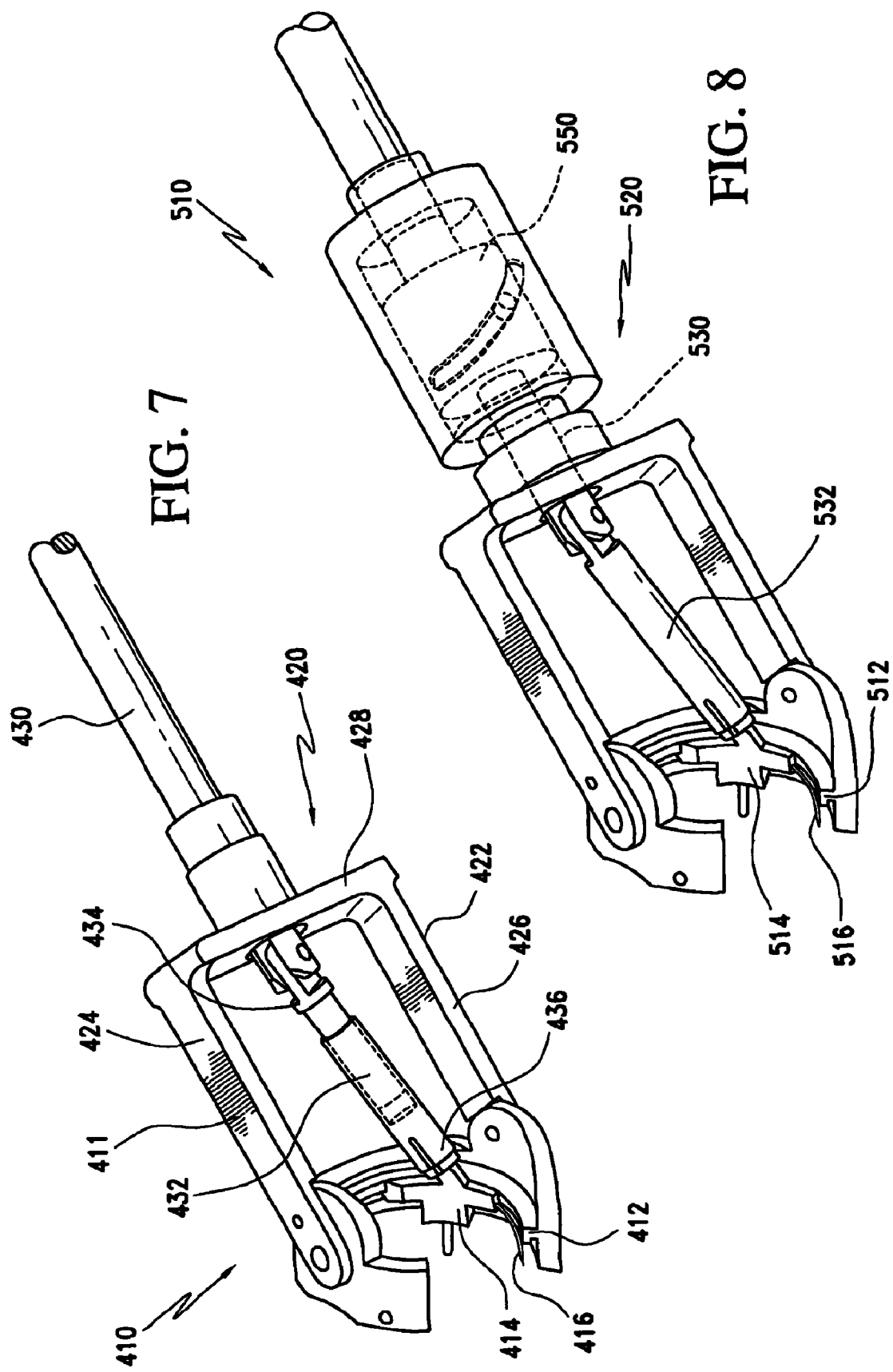

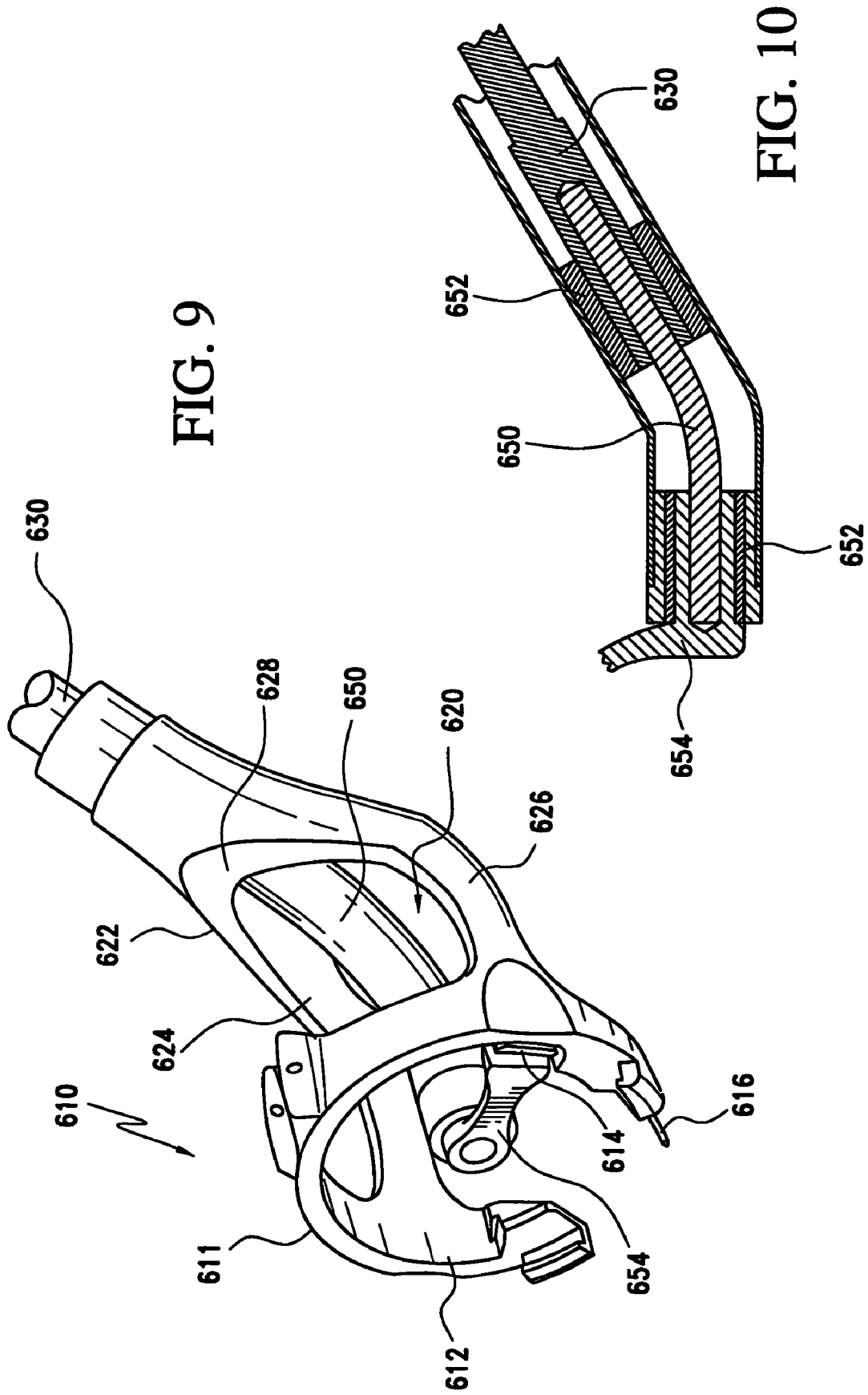

SUTURING DEVICE WITH ANGLED HEAD

BACKGROUND OF THE INVENTION

1. Field of the Invention

The present invention relates to surgical instruments. More particularly, the invention relates to suturing apparatuses for continuous suture application.

2. Description of the Prior Art

With the development of smaller and more reliable motors and associated control mechanisms, the traditional manual technique of soft tissue (fascia) closure has been automated with the development of various automated suturing apparatuses. However, these devices commonly exhibit shortcomings in ergonomics. In particular, the suturing head of these devices is commonly in line with, or perpendicular to, the support shaft upon which the suturing head is mounted. As such, a surgeon, or other medical practitioner, using the device is forced to orient his or her arm in unusual and undesirable orientations to complete the closure of soft tissue.

As such, a more ergonomic suturing apparatus is needed. The present invention provides such a suturing apparatus through the provision of a suturing apparatus in which the suturing head is obliquely oriented relative to the support shaft. This allows a surgeon using the present suturing apparatus better access to a surgical site without the need for the surgeon to orient his or her body in an undesirable, and potentially unsafe, position.

SUMMARY OF THE INVENTION

It is, therefore, an object of the present invention to provide a suturing apparatus for the continuous application of a suture. The apparatus includes a suturing head shaped and dimensioned for attachment to a distal end of a support member, the suturing head including a track shaped and dimensioned for receiving a needle for movement about the track. A support arm includes first and second lateral arms connected by a central connecting member supporting the track, wherein the support arm includes a longitudinal axis and the track lies in a transverse plane. Angular orientation of the support arm relative to the track is achieved by positioning the transverse plane of the track at an oblique angle relative to the longitudinal axis of the support arm such that operators are provided with improved access to the surgical site. A drive assembly is coupled to the needle for controlled movement about the track.

It is also an object of the present invention to provide a suturing apparatus including a sled to which the needle is secured, wherein the sled is shaped and dimensioned for movement about the track and the needle is secured to the sled such that it may be moved about the track under the control of a drive assembly.

It is also another object of the present invention to provide a suturing apparatus wherein the support arm is U-shaped.

It is also a further object of the present invention to provide a suturing apparatus wherein the support arm includes first and second lateral arms connected by a central connecting member supporting the track, and the longitudinal axis of the support arm extends generally parallel to the first and second lateral arms.

It is also an object of the present invention to provide a suturing apparatus wherein the track is oriented at up to approximately a 45-degree angle relative to the longitudinal axis of the final drive shaft.

It is another object of the present invention to provide a suturing apparatus wherein the drive assembly includes a drive shaft which includes a longitudinal axis which is obliquely oriented relative to the transverse plane of the track.

It is a further object of the present invention to provide a suturing apparatus wherein the drive shaft rotates and is pivotally connected to a drive arm extending to the needle for pivotal attachment thereto.

It is still another object of the present invention to provide a suturing apparatus wherein the drive arm is provided with a telescoping joint accommodating adjustments in length.

It is yet another object of the present invention to provide a suturing apparatus wherein the drive shaft oscillates back and forth allowing for changing length as the needle is driven about the track.

It is also an object of the present invention to provide a suturing apparatus wherein the drive assembly and the drive shaft are of a fixed length.

It is a further object of the present invention to provide a suturing apparatus wherein the drive assembly includes a barrel cam on the drive shaft for controlling axial motion of the drive shaft relative to the needle.

It is yet a further object of the present invention to provide a suturing apparatus wherein the drive shaft includes a telescoping joint.

It is also an object of the present invention to provide a suturing apparatus wherein the drive assembly includes a flexible drive shaft.

It is also another object of the present invention to provide a suturing apparatus including a trigger assembly linked to the drive assembly.

It is also a further object of the present invention to provide a suturing apparatus wherein the trigger assembly includes a first pivotally mounted trigger handle.

It is another object of the present invention to provide a suturing apparatus wherein the trigger assembly includes first and second pivotally mounted trigger handles.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 1 is a perspective view of a suturing apparatus in accordance with a first embodiment.

FIG. 2 is a detailed perspective view of the suturing head of the suturing apparatus shown in FIG. 1.

FIG. 7 is a detailed perspective view of an alternate suturing head in accordance with the present invention.

FIG. 8 is a detailed perspective view of another suturing head which may be employed in accordance with the present invention.

FIG. 9 is a detailed perspective view of yet another suturing head which may be employed in accordance with the present invention.

FIG. 10 is a detailed cross sectional view showing the drive assembly of the embodiment shown with reference to FIG. 9.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to the various embodiments shown in FIGS. 1 to 10, a suturing apparatus for the continuous application of a suture is disclosed. Although the suturing apparatus is particularly adapted for use in performing soft tissue (fascia) procedures, those skilled in the art will certainly appreciate the apparatus may be used for a wide variety of applications without departing from the spirit of the present invention. In general, the suturing apparatus includes a suturing head that is shaped and dimensioned for attachment to the distal end of a support member. The suturing head is oriented relative to the support member in a manner which improves upon the ergonomics of the suturing apparatus.

Figure 3:
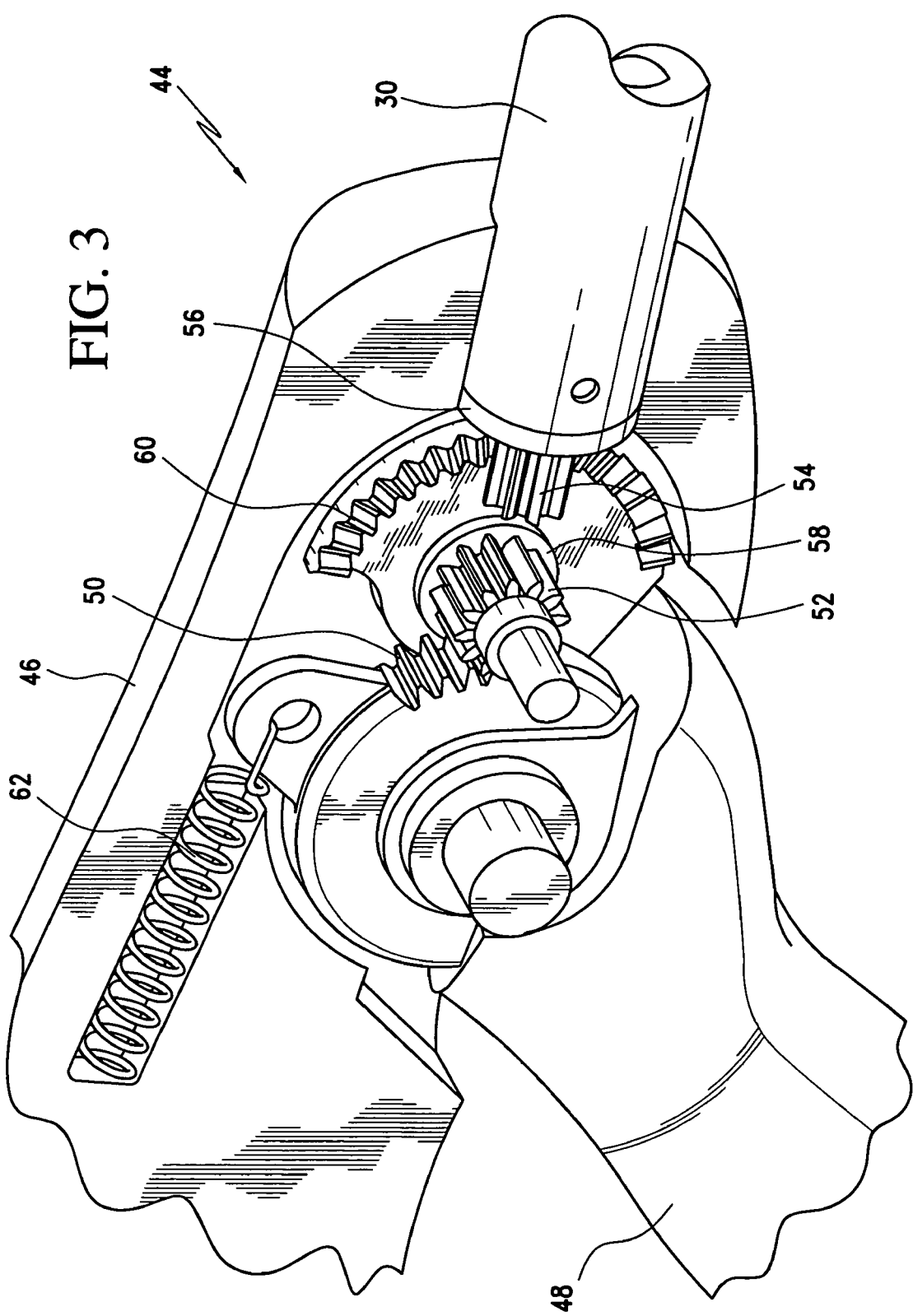
FIG. 3 is a detailed view showing the trigger assembly employed in accordance with the embodiment show in FIG. 1.

In accordance with a first embodiment, and with reference to FIGS. 1, 2 and 3, the suturing apparatus 10 includes a suturing head 11 that has a track 12 shaped and dimensioned for receiving and supporting a sled 14 to which a needle 16 is selectively secured for circular movement about the track 12. The sled 14 is shaped and dimensioned for reciprocating movement about the track 12 in which it is mounted for free movement in accordance with the present invention. The needle 16 is releasably secured to the sled 14 such that it may be moved about the track 12 in a circular motion under the control of the drive assembly 20. The track 12 is shaped and dimensioned for supporting and guiding the sled 14 and needle 16 positioned therein for movement of the needle 16 about a predetermined circular path under the control of the drive assembly 20.

Movement of the needle 16 is achieved by the reciprocating movement of the sled 14 upon the track 12 in a manner such that when the sled 14 is moved in a first direction it pushes the needle 16 across an opening 63 in the suturing head 11. Pushing of the needle 16 in this manner continues until the sled 14 reaches a first position adjacent a first end 64 of the track 12. The sled 14 then releases the needle 16 and rotates about the track 12 in a second direction to a second position adjacent the second end 66 of the track 12 where it reengages with the needle 16 for repeating of the circular motion of the needle 16. In accordance with a preferred embodiment, and as will be discussed below in greater detail, the needle 16 is driven about an arc of approximately 180 to 195 degrees with each actuation of the sled 14. The interaction of the sled 14 with the needle 16 for accomplishing the pushing and releasing disclosed above is preferably achieved through the utilization of notches or other engagement surfaces along the needle that selectively engage the sled in a manner similar to that disclosed in commonly owned U.S. patent application Ser. No. 11/394,163, entitled "Surgical Suturing Apparatus With Collapsible Vacuum Chamber", filed Mar. 31, 2006, which is incorporated herein by reference.

A U-shaped support arm 22, including first and second lateral arms 24, 26 connected by a central connecting member 28, supports the track 12. In accordance with a preferred embodiment, the support arm 22 includes a longitudinal axis extending generally parallel to the first and second lateral arms 24, 26. The track 12 lies in a transverse plane obliquely oriented relative to the longitudinal axis of the support arm 22. Angular orientation of the support arm 22 relative to the track 12 is achieved by positioning the transverse plane of the track 12 at an oblique angle relative to the longitudinal axis of the support arm 22. By angularly orienting the track 12 relative to the support arm 22, operators are provided with improved access to the surgical site.

In accordance with a preferred embodiment of the present invention, the transverse plane of the track 22 is oriented at up to approximately a 45-degree angle relative to the longitudinal axis of the support arm 22. While a preferred angular orientation is disclosed in accordance with a preferred embodiment of the present invention, those skilled in the art will appreciate the angular orientation may be varied to suit specific applications without departing from the spirit of the present invention. Referring to the drive assembly 20, which is utilized in moving the needle 16 about the track 12 while the track 12 is obliquely oriented relative to the support arm 22 and ultimately the drive assembly 20, it extends from, and is actuated by, a trigger assembly 44 and is linked to the sled 14 and needle 16 for continuously driving the needle 16 about the track 12. In particular, the drive assembly 20 is specifically designed such that it is able to fully drive the needle 16 about the predetermined circular path regardless of the orientation of the track 12.

The drive assembly 20 of the present suturing device 10 allows the needle 16 to be moved in a circular pattern while being on an oblique angle relative to the drive shaft 30 of the drive assembly 20. That is, the drive shaft 30 includes a longitudinal axis which is obliquely oriented relative to the transverse plane in which the track 12 lies and the needle 16 moves. This contrasts with currently available devices that require the needle be substantially perpendicular to the drive shaft of the drive assembly.

In accordance with the present invention, the trigger assembly 44 that attaches to the proximal end of the drive shaft 30 drives the needle 16 via movement of the sled 14 approximately 180 to 195 degrees with each actuation of a trigger handle 48. Upon tilting the needle 16 to an acute angle relative to the drive shaft 30, the distance from the needle 16 to the drive shaft 30 changes as a result of the circular motion needed to drive the needle 16. This is addressed by the present drive assembly 20 discussed below in greater detail.

The drive system 20 includes a rotating drive shaft 30 pivotally connected to a drive arm 32 extending to the sled 14 for pivotal attachment thereto. More particularly, the drive arm 32 includes a first end 34 and a second end 36. The first end 34 is pivotally connected to the rotating drive shaft 30 of the drive system 20, while the second end 36 is pivotally connected to the sled 14.

In accordance with a preferred embodiment, a single pivot joint 38 is used in connecting the first end 34 of the drive arm 32 to the rotating drive shaft 30. In particular, the pivot joint 38 connecting the drive arm 32 to the rotating drive shaft 30 extends substantially perpendicular to both the longitudinal axis of the rotating drive shaft 30 and the drive arm 32.

With regard to the connection of the second end 36 of the drive arm 32 to the sled 14, a multiple axis joint 40 is employed. For example, and in accordance with a preferred embodiment of the present invention, a ball and socket joint 40 connects the drive arm 32 to the sled 14. In accordance with this embodiment, the drive arm 32 connected to the sled 14 is of a fixed length and the drive shaft 30 oscillates back and forth allowing for changing length as the sled 14 and the needle 16 follow the track 12 around the drive mount. Given the drive shaft 30 must adjust its length, the drive shaft 30 includes a telescoping joint 42 accommodating adjustments in length.

The drive system 20 further includes a trigger assembly 44 linked to the drive shaft 30 for translating trigger motion thereof to rotational motion of the drive shaft 30 in a manner moving the needle 16 about its circular path. More particularly, and with reference to FIG. 3, a preferred embodiment of a trigger assembly 44 for driving the drive shaft 30 is disclosed. The trigger assembly 44 includes a housing 46 with a pivotally mounted trigger handle 48 secured thereto. The trigger handle 48 is linked to a crank gear 50. The crank gear 50 is linked to an input gear 52, which is ultimately linked to a crown gear 54 at the distal end 56 of the drive shaft 30 via a hypoid gear 60. As such, by regularly actuating the trigger handle 48, the transmission, which is composed of the crank gear 50, the input gear 52 and the crown gear 54, one is able to create rotational movement within the drive shaft 30 which is ultimately translated to the needle 16.

Oscillatory cranking of the trigger handle 48 to create reciprocating movement of the sled 14 is achieved by the use of a fixed link 58 between the input gear 52 and the hypoid gear 60 such that rotational movement is transmitted to the crown gear 54 when the trigger handle 48, and ultimately the input gear 52, are moved back and forth via the actuation of the trigger handle 48. Further, a spring 62 is connected to the trigger handle 48 for returning it to its starting position after each actuation thereof.

Figure 4:
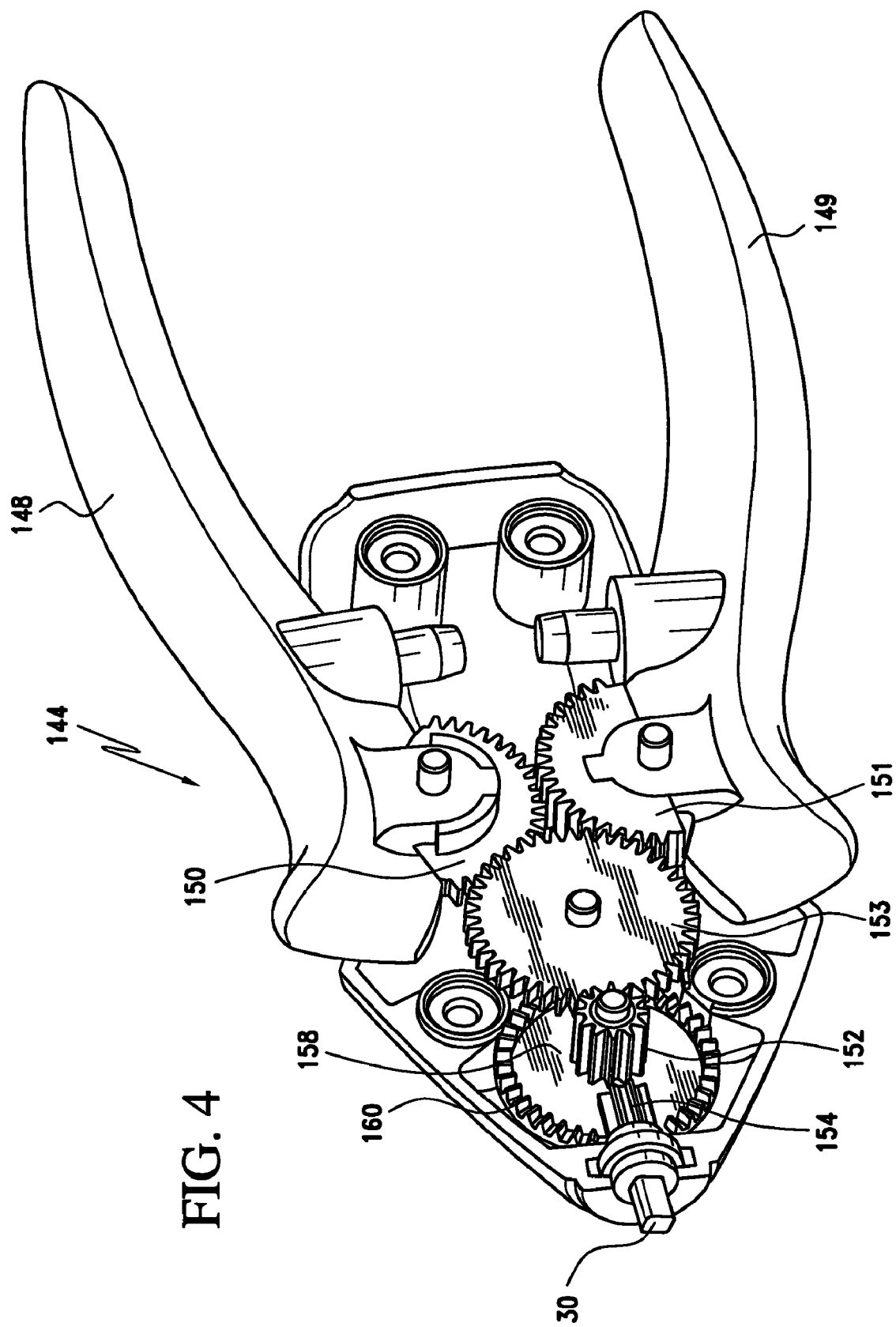
FIGS. 4, 5 and 6 show various alternate trigger assemblies that may be employed in accordance with a preferred embodiment of the present invention.

With reference to FIG. 4, an alternate trigger assembly 144 is disclosed. This trigger assembly 144 includes first and second pivotally mounted trigger handles 148, 149. Each trigger handle 148, 149 includes a crank gear 150, 151 which is linked to an input gear 153, which is linked to a secondary input gear 152, which is ultimately linked to the crown gear 154 that transmits rotational energy to the drive shaft 30 via a hypoid gear 160. By utilizing dual trigger handles 148, 149, as disclosed in accordance with this invention, pressure upon the hand is reduced and greater control is achieved. As with the prior embodiment, a fixed link 158 is positioned between the secondary input gear 152 and the hypoid gear 160 such that reciprocating rotational movement is transmitted to the crown gear 154 when the trigger handle 148, and ultimately the secondary input gear 152, are moved back and forth via actuation of the trigger handles 148, 149. In addition, each trigger handle 148, 149 is coupled to a spring (not shown) for returning it to its starting position after each actuation.

Figure 5:
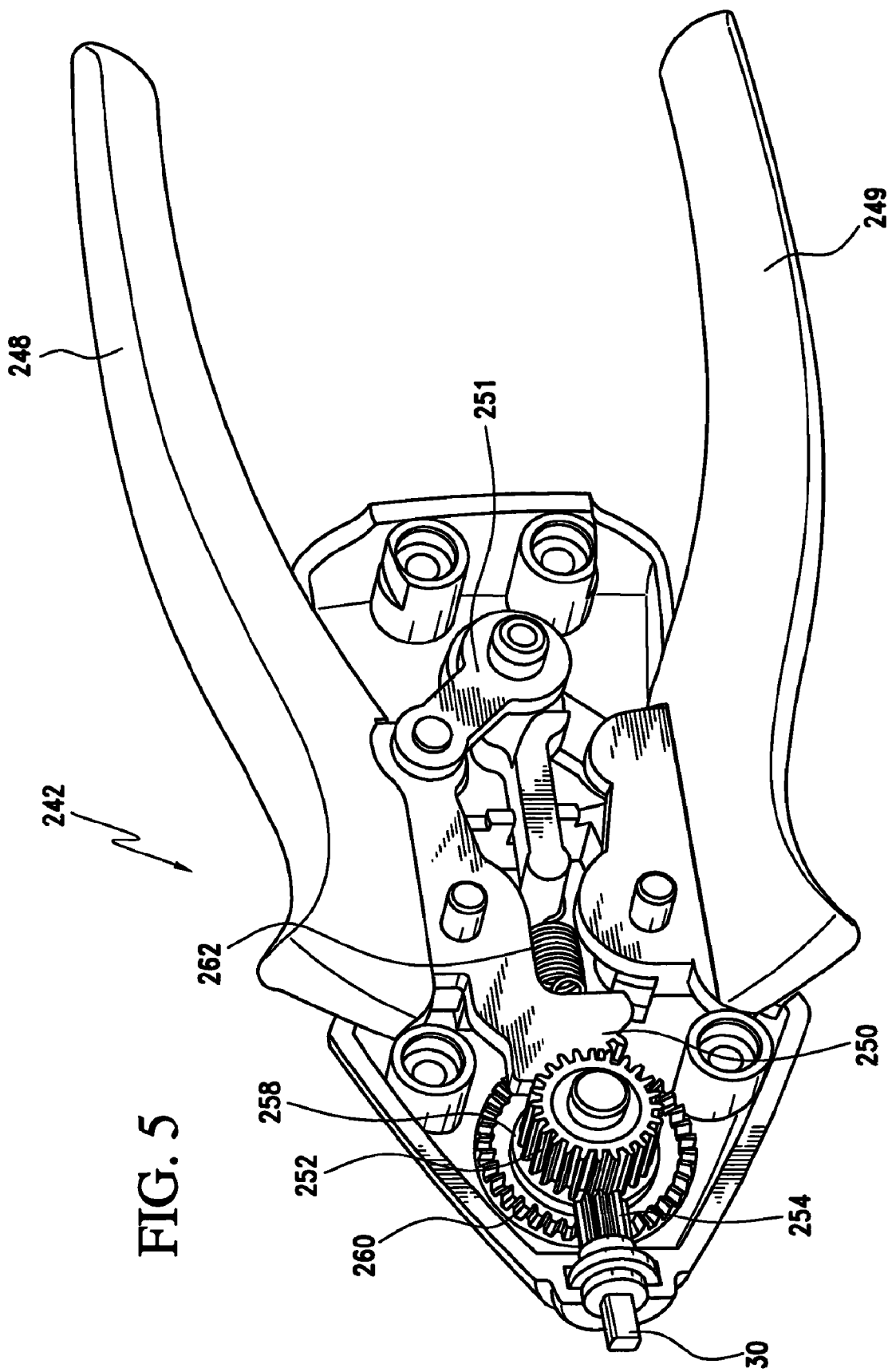

A further embodiment is disclosed with reference to FIG. 5. This trigger assembly 242 includes first and second pivotally mounted trigger handles 248, 249. The first trigger handle 248 includes an extending crank gear 250 linked to an input gear 252, which is ultimately linked to the crown gear 254 that transmits rotational energy to the drive shaft 30 via a hypoid gear 260. Actuation assistance is achieved by linking the second trigger handle 249 to the first trigger handle 248 via a linkage mechanism 251. As a result, pressure applied to the second trigger handle 249 is transferred to the first trigger handle 248, and ultimately the crank gear 250 extending from the first trigger handle 248. By utilizing dual trigger handles 248, 249 as disclosed in accordance with this invention, pressure upon the hand is reduced and greater control is achieved. As with the prior embodiment, each trigger handle 248, 249 is coupled to a spring 262 for returning it to its starting position after each actuation. Regular reciprocating actuation of the trigger handles 248, 249 for the production of reciprocating movement in the sled is achieved by the inclusion of a fixed link 258 between the input gear 252 and the hypoid gear 260.

Figure 6:
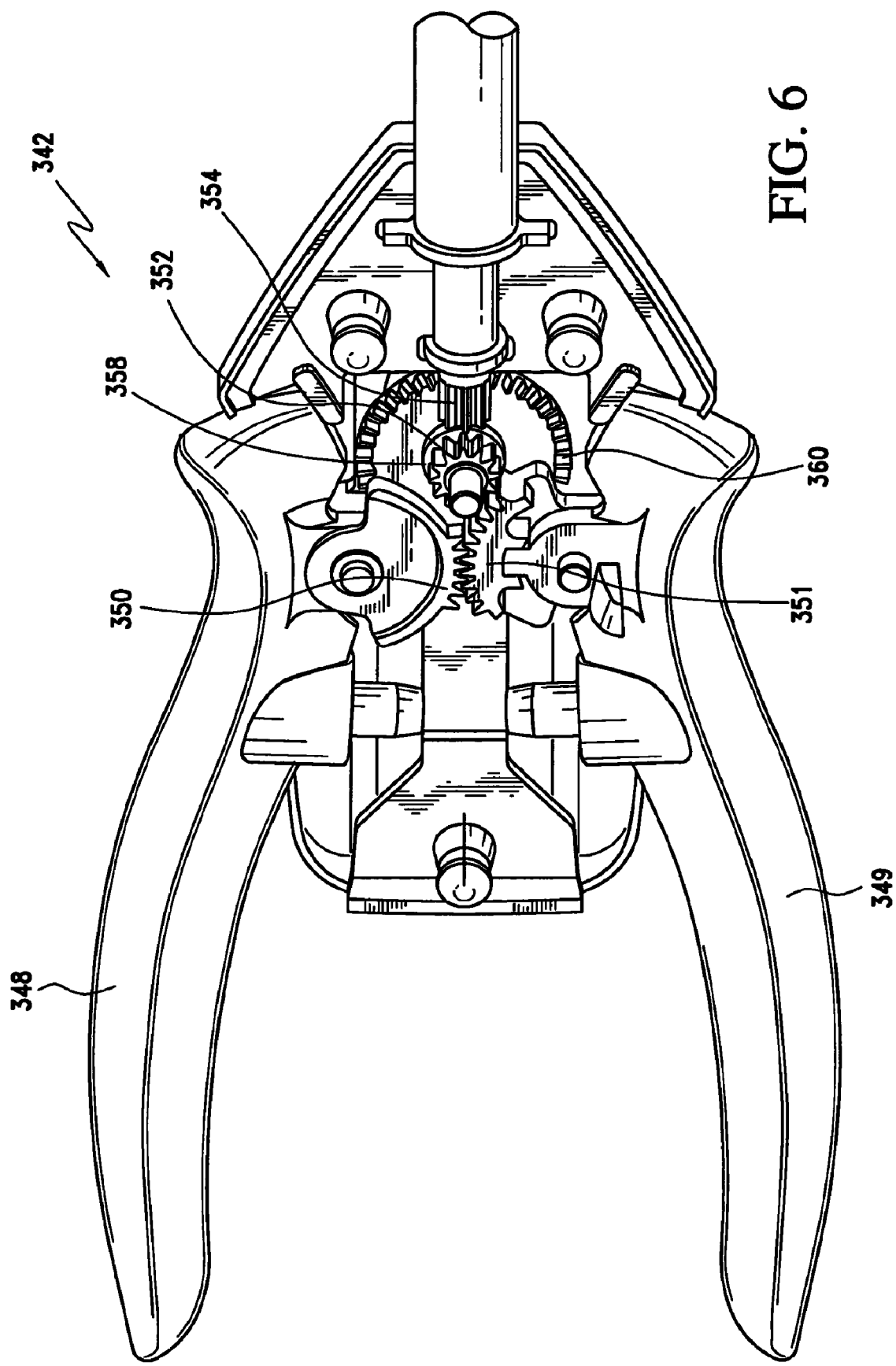

With reference to FIG. 6, a further embodiment of a trigger assembly 342 is disclosed. This trigger assembly 342 includes first and second pivotally mounted trigger handles 348, 349. Each trigger handle 348, 349 includes a crank gear 350, 351. The crank gear 350 of the first trigger handle 348 is linked to the crank gear 351 of the second trigger handle 351 which is ultimately linked to an input gear 352. The input gear 352 is ultimately linked to the crown gear 354 that transmits rotational energy to the drive shaft 30. By utilizing dual trigger handles 348, 349 as disclosed in accordance with this invention, pressure upon the hand is reduced and greater control is achieved. As with the prior embodiment, a fixed link 358 is positioned between the input gear 352 and the hypoid gear 360 such that reciprocating rotational movement is transmitted to the crown gear 354 when the trigger handles 348, 349, and ultimately the input gear 352, are moved back and forth during actuation of the trigger handles 348, 349. In addition, each trigger handle 348, 349 is coupled to a spring (not shown) for returning it to its starting position after each actuation.

As those skilled in the art will certainly appreciate, a variety of trigger mechanisms may be employed without departing from the spirit of the present invention.

In accordance with an alternate embodiment, and with reference to FIG. 7, a similar structure is disclosed for driving a needle 416 about an angularly oriented track 412. As with the prior embodiment, the suturing head 411 includes a sled 414 riding upon a track 412 formed thereon. The track 412 is shaped and dimensioned for supporting and guiding the needle 416 positioned therein for movement about a predetermined circular path under the control of the drive assembly 420 in the manner described above with reference to FIGS. 1 to 3. A U-shaped support arm 422, including first and second lateral arms 424, 426 connected by a central connecting member 428, supports the track 412. Angular orientation of the support arm 422 relative to the track 412 is achieved by positioning the transverse plane of the track 412 at an oblique angle relative to the longitudinal axis of the support arm 422. By angularly orienting the track 412 relative to the support arm 422, operators are provided with improved access to the surgical site.

The drive assembly 420 includes a rotating drive shaft 430 pivotally connected to a drive arm 432 extending to the sled 414 for pivotal attachment thereto. More particularly, the drive arm 432 includes a first end 434 and a second end 436. The first end 434 is pivotally connected to the rotating drive shaft 430 of the drive assembly 420, while the second end 436 is pivotally connected to the sled 414. As with the embodiment disclosed with reference to FIGS. 1 to 3, the drive assembly 420 is linked to a trigger assembly adapted to drive the drive shaft 430 for rotational movement.

In accordance with this embodiment, the drive arm 432 is connected to the sled 414 and needle 416. The drive arm 432 oscillates back and forth allowing for changing length as the needle 416 follows the track 412 around the drive mount. Given that length adjustment is required to accommodate movement of the needle 416, the drive arm 432 is provided with a telescoping joint 442 accommodating adjustments in length. More particularly, the drive arm 432 includes a telescoping structure allowing the drive arm 432 to change its length as it moves the sled 414 and needle 416 about the track 412 while the drive shaft 430 remains in a fixed position.

In accordance with yet a further embodiment, and with reference to FIG. 8, the suturing apparatus 510 includes basic structure substantially similar to that disclosed above with reference to FIGS. 1-3 and 7. However, the drive assembly 520 employs a drive shaft 530 and drive arm 532 which are of a fixed length. The drive shaft 530 rotates the drive arm 532 to actuate the needle 516 about the track 512 in manner described above with reference to FIGS. 1 to 3. However, this embodiment employs a barrel cam 550 on the drive shaft 530 to control the axial motion of the drive shaft 530 relative to the sled 514. This frees the sled 514 and track 512 from the forces needed to position the drive shaft 530 at a desired orientation for driving the needle 516 thereabout. As with the embodiment disclosed with reference to FIGS. 1 to 3, the drive assembly 520 is linked to a trigger assembly adapted to drive the drive shaft 530 for rotation movement.

In accordance with an alternate embodiment, and with reference to FIGS. 9 and 10, similar structure is disclosed for driving a needle 616 about an angularly oriented track 612. As with the prior embodiments, the suturing head 611 includes a sled 614 riding upon the track 612 formed thereon. The track 612 is shaped and dimensioned for supporting and guiding the needle 616 positioned thereon for movement about a predetermined circular path under the control of the drive assembly 620 in the manner described above with reference to FIGS. 1 to 3. A U-shaped support arm 622, including first and second lateral arms 624, 626 connected by a central connecting member 628 supports the track 612. Angular orientation of the support arm 622 relative to the track 612 is achieved by positioning the transverse plane of the track 612 at an oblique angle relative to the longitudinal axis of the support arm 622. By angularly orienting the track 612 relative to the support arm 622, operators are provided with improved access to the surgical site.

The drive assembly 620 includes a flexible drive cable 650 extending from the drive shaft 630. The flexible drive cable 650 is supported by bearings 652 located proximally and distally of the bend portion. The distal end of the flexible drive cable 650 is connected to a drive pawl 654, which in turn drives the needle 616 about the track 612.

In accordance with the present invention, each of the various embodiments disclosed above may be provided with an anti-backup system for controlling movement of the needle. Such a system is disclosed in commonly owned U.S. patent application Ser. No. 11/394,161, entitled "Surgical Suturing Apparatus With Anti-Backup System, filed Mar. 31, 2006, which is incorporated herein by reference. Briefly, these anti-backup structures disclosed in the '161 application control needle movement so the needle is only allowed to pass in one direction. This prevents the needle from backing out between actuating strokes. More particularly, the needle of the present suturing apparatus is designed to move in a predetermined first direction about an arcuate path, and movement in an opposite second direction is undesired. As such, the present anti-backup structures prevent movement of the needle in the second direction while permitting free movement of the needle in the first direction.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A suturing apparatus for the continuous application of a suture, comprising:
   a suturing head shaped and dimensioned for attachment to a distal end of a support member, the suturing head including a track shaped and dimensioned for supporting and guiding the needle for movement in a predetermined circular path under the control of a drive assembly;
   a support arm including first and second lateral arms connected by a central connecting member supporting the track, wherein the support arm includes a longitudinal axis and the track and needle lie in a transverse plane, angular orientation of the support arm relative to the track and needle is achieved by positioning the transverse plane of the track at an oblique angle relative to the longitudinal axis of the support arm such that the needle is moved about a circular pattern while being on an oblique angle relative to the longitudinal axis of the support arm thereby providing operators with improved access to the surgical site; and
   the drive assembly coupled to the needle for driving the needle about the predetermined circular path under the guidance of the track, the drive assembly includes a drive shaft including a longitudinal axis in parallel alignment with the longitudinal axis of the support arm, the drive shaft rotating about the longitudinal axis thereof.

2. The suturing apparatus according to claim 1, further including a sled to which the needle is secured, wherein the sled is mounted on the track for movement about the track and the needle is secured to the sled such that it may be moved about the track under the control of the drive assembly.

3. The suturing apparatus according to claim 1, wherein the support arm is U-shaped.

4. The suturing apparatus according to claim 3, wherein the support arm includes first and second lateral arms connected by the central connecting member supporting the track, and the longitudinal axis of the support arm extends generally parallel to the first and second lateral arms.

5. The suturing apparatus according to claim 1, wherein the track is oriented at up to approximately a 45-degree angle relative to the longitudinal axis of the drive shaft.

6. The suturing apparatus according to claim 1, wherein the longitudinal axis of the drive shaft is obliquely oriented relative to the transverse plane of the track.

7. The suturing apparatus according to claim 6, wherein the drive shaft rotates and is pivotally connected to a drive arm extending to the needle for pivotal attachment thereto.

8. The suturing apparatus according to claim 7, wherein the drive arm is provided with a telescoping joint accommodating adjustments in length.

9. The suturing apparatus according to claim 7, wherein the drive shaft oscillates back and forth allowing for changing length as the needle is driven about the track.

10. The suturing apparatus according to claim 7, wherein the drive assembly and the drive shaft are of a fixed length.

11. The suturing apparatus according to claim 10, wherein the drive assembly includes a barrel cam on the drive shaft for controlling axial motion of the drive shaft relative to the needle.

12. The suturing apparatus according to claim 6, wherein the drive shaft oscillates back and forth allowing for changing length as the needle is driven about the track.

13. The suturing apparatus according to claim 12, wherein the drive shaft includes a telescoping joint.

14. The suturing apparatus according to claim 1, wherein the drive assembly includes a flexible drive shaft.

15. The suturing apparatus according to claim 1, further including a trigger assembly linked to the drive assembly.

16. The suturing apparatus according to claim 15, wherein the trigger assembly includes a first pivotally mounted trigger handle.

17. The suturing apparatus according to claim 15, wherein the trigger assembly includes first and second pivotally mounted trigger handles.

18. The suturing apparatus according to claim 2, wherein the sled is releasably secured to the needle.

* * * * *